(12) United States Patent
Hoyt

(10) Patent No.: US 8,020,460 B1
(45) Date of Patent: Sep. 20, 2011

(54) SENSOR HOUSING AND MOUNT FOR IN-LINE INSPECTION TOOL

(76) Inventor: Philip M. Hoyt, Murray, UT (US)

( * ) Notice: Subject to any disclaimer, the term of this patent is extended or adjusted under 35 U.S.C. 154(b) by 112 days.

(21) Appl. No.: 12/403,754

(22) Filed: Mar. 13, 2009

Related U.S. Application Data

(63) Continuation-in-part of application No. 12/258,365, filed on Oct. 24, 2008, now abandoned.

(60) Provisional application No. 61/065,455, filed on Feb. 11, 2008.

(51) Int. Cl.
*G01M 99/00* (2006.01)
(52) U.S. Cl. ............... 73/865.8; 324/220; 73/866.5
(58) Field of Classification Search ............ 73/40.5, 73/623, 866.5; 324/220–221
See application file for complete search history.

(56) References Cited

U.S. PATENT DOCUMENTS

| | | | |
|---|---|---|---|
| 3,543,144 A * | 11/1970 | Walters et al. | 324/221 |
| 3,786,684 A | 1/1974 | Wiers et al. | |
| 3,949,292 A | 4/1976 | Beaver et al. | |

(Continued)

FOREIGN PATENT DOCUMENTS

WO   WO 2006067369 A1 *   6/2006

OTHER PUBLICATIONS

BJ Pipeline Inspection Services, Sales Brochure, BJ Process and Pipeline Services, a division of BJ Services Company, Houston, TX, 2003.

(Continued)

*Primary Examiner* — Hezron E Williams
*Assistant Examiner* — Nashmiya Fayyaz
(74) *Attorney, Agent, or Firm* — Warren M. Pate, LLC

(57) ABSTRACT

An in-line inspection tool comprising sensors and sensor housings is disclosed. Each sensor housing may contain at least one sensor. The tool may further comprise a structure comprising a central axis and a plurality of sensor mounts distributed circumferentially about the central axis. Each sensor mount may support a different sensor housing. The plurality of sensor mounts may support the sensor housings such that the first end of each sensor housing circumferentially overlaps the second end of an adjacent sensor housing. By overlapping, sensor housings may support sensors with substantially uniform spacing around the circumference of the inspection tool in normal operation and still allow sensor housings to move relative to one another to accommodate changes in the dimension of the circumference.

16 Claims, 5 Drawing Sheets

U.S. PATENT DOCUMENTS

| | | | |
|---|---|---|---|
| 3,967,194 | A | 6/1976 | Beaver et al. |
| 4,105,972 | A | 8/1978 | Smith |
| 4,447,777 | A | 5/1984 | Sharp et al. |
| 4,769,598 | A | 9/1988 | Krieg et al. |
| 4,883,191 | A | 11/1989 | Christensen |
| 5,000,333 | A | 3/1991 | Petrelli |
| 5,359,939 | A * | 11/1994 | Watt ............................ 104/138.2 |
| 5,371,363 | A * | 12/1994 | Lilimpakis .................... 250/253 |
| 5,454,276 | A | 10/1995 | Wernicke |
| 5,565,633 | A | 10/1996 | Wernicke |
| 5,850,935 | A | 12/1998 | Luburic et al. |
| 5,864,232 | A | 1/1999 | Laursen |
| 6,023,986 | A | 2/2000 | Smith et al. |
| 6,087,830 | A | 7/2000 | Brandly et al. |
| 6,107,795 | A | 8/2000 | Smart |
| 6,198,277 | B1 | 3/2001 | Porter et al. |
| 6,232,773 | B1 | 5/2001 | Jacobs et al. |
| 6,538,431 | B2 | 3/2003 | Couchman et al. |
| 6,640,655 | B1 | 11/2003 | Manzak et al. |
| 6,720,855 | B2 | 4/2004 | Vicci |
| 6,847,207 | B1 | 1/2005 | Veach et al. |
| 7,256,576 | B2 | 8/2007 | Mandziuk et al. |
| 7,374,066 | B2 | 5/2008 | Jackson et al. |
| 7,407,115 | B2 | 8/2008 | Laidler |
| 7,416,097 | B2 | 8/2008 | Crisp, III et al. |
| 7,548,059 | B2 | 6/2009 | Thompson et al. |
| 2003/0136195 | A1 * | 7/2003 | Krieg et al. ..................... 73/628 |
| 2006/0248966 | A1 | 11/2006 | Houldey et al. |

OTHER PUBLICATIONS http://www.bjservices.com/website/index.nsf/P&S?openframeset , Process and Pipeline Services, Pipeline Inspection Services, Vectra MFL Tool.

Pipeline Operator Assists in new ILI tool development, Tech Notes: Product Development, Marathon Ashland Pipe Line LLC, Pipeline & Gas Journal, Dec. 1, 2001.

Recent Developments in Multi-diameter Inspection Tool Technologies, Kjartan Vartdal and Kjell Traa, PipeCare AS, Stavanger, Norway, The Pipeline Pigging, Integrity Assessment and Repair Conference, Houston, TX, Feb. 5-6 , 2003.

* cited by examiner

SENSOR HOUSING AND MOUNT FOR IN-LINE INSPECTION TOOL

RELATED APPLICATIONS

This application is a continuation-in-part of U.S. patent application Ser. No. 12/258,365 filed Oct. 24, 2008 now abandoned, which claims the benefit of U.S. Provisional Patent Application Ser. No. 61/065,455 filed Feb. 11, 2008.

BACKGROUND

1. Field of the Invention

This invention relates to pipeline inspection tools, and more particularly to apparatus and methods for housing and mounting sensors for use on an in-line inspection tool.

2. Background of the Invention

Oil, petroleum products, natural gas, hazardous liquids, and the like are often transported using pipelines. The majority of these pipelines are constructed from steel pipe. Once installed, a pipeline will inevitably corrode or otherwise degrade. Proper pipeline management requires identification, monitoring, and repair of defects and vulnerabilities of the pipeline. For example, information collected about the condition of a pipeline may be used to determine safe operating pressures, facilitate repair, schedule replacement, and the like.

Typical defects of a pipeline may include corrosion, gouges, dents, and the like. Corrosion may cause pitting or general wall loss, thereby lowering the maximum operating pressure of the pipeline. Vulnerabilities may also include curvature and bending anomalies, which may lead to buckling, and combined stress and chemical or biological action such as stress corrosion cracking. Without detection and pre-emptive action, all such defects and vulnerabilities may lead to pipeline failure.

Information on the condition of a pipeline is often collected using an in-line inspection tool. An in-line inspection tool typically uses sensors to collect information about a pipeline as it travels therethrough. In the past, in-line inspection tools have used magnetic flux leakage to determine the condition of a pipeline wall. Flaws in ferromagnetic pipe can be detected by the perturbations they cause in a magnetic field applied to the wall of a pipeline. Changes in the magnetic field generate signals that are detected by the sensors, processed, and recorded on a device such as a computer hard drive or flash memory carried on the inspection vehicle. Accordingly, in-line inspection tools typically include computer hardware, power sources, and the like.

To collect useful data, the sensors carried by an in-line inspection tool must closely track the interior surface of the pipe being inspected. They are typically mounted in sensor housings that hold them around the circumference of the inspection tool in groups of one or more sensors. However, the interior surfaces of pipes are not uniform and the sensor housings must move relative to one another as the tool passes sections with varying interior surfaces. This movement often results in non-uniform sensor spacing.

In the past, non-uniform sensor spacing has been deemed inconsequential because the magnetic field applied to the wall of a pipe spreads circumferentially. Anomalies are detected by the sensors even when the sensors do not track directly over the inconsistencies. However, non-uniform sensor spacing cannot produce uniform inspection of the pipe wall and an incorrect picture of irregularities in the pipe wall must result. Relative deviation from the actual condition is more consequential as sensors are placed more closely together. Accordingly, what is needed is a system for housing and mounting sensors that accommodates the variability of the interior surfaces of pipes while maintaining proper uniform sensor distribution.

SUMMARY

An in-line inspection tool and associated methods in accordance with the present invention may comprise or utilize various components including a plurality of inspection assemblies. The inspection assemblies may be distributed circumferentially about the tool. Each inspection assembly may include a sensor housing. Each sensor housing may contain and protect one or more sensors and their associated circuitry from a pipeline environment. A sensor mount may connect each sensor housing to the rest of the inspection assembly.

Inspection assemblies may move in a radial direction with respect to the main body of an in-line inspection tool. This freedom of motion may accommodate changes in the pipe being inspected. For example, features such as bends, constrictions, and changes in the thickness of the wall of the pipe may all affect the interior diameter of a pipeline. Radial movement of an inspection assembly may permit a sensor housing to closely track the interior surface of a pipeline in spite of changes in the interior diameter thereof.

Movement in a radial direction changes the spacing in the circumferential direction between adjacent inspection assemblies. An inspection assembly in accordance with the present invention may be configured to preserve inspection quality and resolution while accommodating the changes in circumferential spacing caused by radial movement. For example, while inspecting a section of pipe having the nominal or expected inner diameter, the spacing between the end sensors of adjacent sensor housings may correspond closely with (i.e., substantially match) the spacing between the sensors within a sensor housing.

Sensor housings may be held adjacent to one another with the first end of one sensor housing circumferentially overlapping the second end of an adjacent sensor housing. For example, a first end of each sensor housing may be tapered toward the leading edge of the sensor housing. The second end of each sensor housing may be tapered toward the trailing edge thereof.

As adjacent sensor housings move inward in a radial direction, they may be urged closer to one another. The force urging the two sensor housings closer together may increase the sensor overlap. In selected embodiments, the abutting surfaces may be specifically designed to permit or even facilitate this additional overlap.

With additional overlap of adjacent sensor housings, each sensor housing may tend to rotate about an axis extending in the radial direction. That is, for sensor housings to slide past one another, each sensor housing may rotate to vacate space into which an adjacent sensor housing may extend. The corresponding angles or tapers of adjacent contacting ends may ensure that each sensor housing rotates in the same direction. While overlap of sensor housings may result in multiple sensors tracking the same portion of pipe, this redundancy in constricted spaces may ensure that sensor coverage in non-constricted spaces is uniformly distributed and complete.

In selected embodiments, a sensor mount may be sufficiently flexible to permit a sensor housing held thereby to rotate about an axis extending in the radial direction in the manner described hereinabove. A sensor mount may also be sufficiently resilient so that after the constriction in the pipe has passed, the sensor mount returns the sensor housing held thereby to its original alignment.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION

Figure 1:
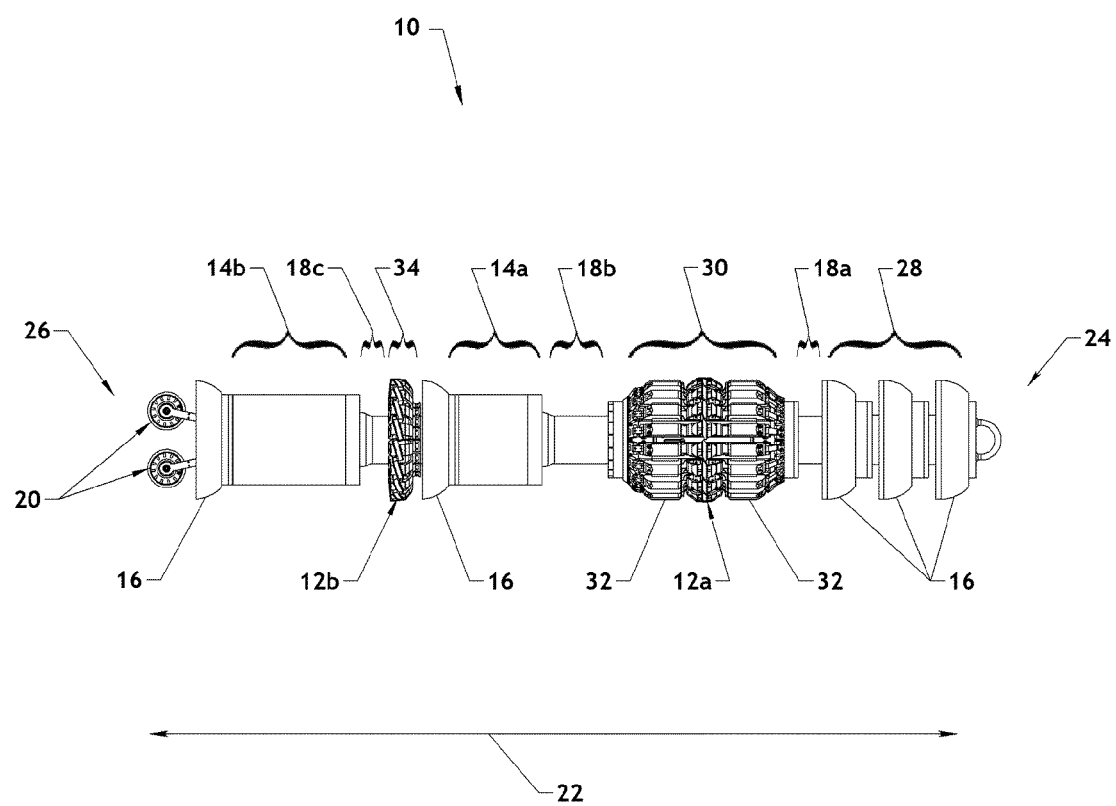
FIG. 1 is an elevation view of one embodiment of an in-line inspection tool in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention as claimed, but is merely representative of various embodiments of the invention. The illustrated embodiments of the invention will be best understood by reference to the drawings, wherein like parts are designated by like numerals throughout.

Referring to FIG. 1, an in-line inspection tool 10 in accordance with the present invention may comprise various components including inspection sensors 12, canisters 14, driving cups 16, couplers 18, position sensors 20, and the like. Canisters 14 may house equipment such as one or more processors, memory devices, and batteries. The driving cups 16 may center the tool 10 within the pipeline and enable fluid traveling within a pipeline to engage the tool 10, thereby pushing the tool 10 through the pipeline. In selected embodiments, driving cups 16 may be formed of a somewhat flexible polyurethane or similar material. Couplers 18 may support bending of the tool 10, enabling the tool 10 to accommodate bends in the pipeline. Like the driving cups 16, in selected embodiments the couplers 18 may be formed of a somewhat flexible polyurethane or similar material or a mechanical pivoting device.

An in-line inspection tool 10 may extend in a longitudinal direction 22 from a head end 24 to a tail end 26. The various components 12, 14, 16, 18, 20 of an in-line inspection tool 10 may be arranged in series. For example, in the illustrated embodiment, the head end 24 of a tool 10 may comprise a head section 28 comprising one or more driving cups 16. Following the head section 28 may be a primary sensor suite 30. In selected embodiments, a primary sensor suite 30 may comprise an array of magnets 32 and sensors 12a. A coupler 18a may extend to connect the head section 28 to the primary sensor suite 30.

Following the primary sensor suite 30 may be a first canister 14a. In one embodiment, the first canister 14a may house the hardware providing the processing and memory storage for the in-line inspection tool 10. A coupler 18b may extend to connect the primary sensor suite 30 to the first canister 14a.

The first canister 14a may be followed by another driving cup 16 and a secondary sensor suite 34. A coupler 18c may engage the second sensor suite 34 and extend rearwardly to engage a second canister 14b. In one embodiment, the second canister 14b may house the batteries providing the power for the in-line inspection tool 10. In selected embodiments, a driving cup 16 may connect to the second canister 14b. One or more position sensors 20 may then engage the second canister 14b, driving cup 16, or some combination thereof to form the tail end 26 of the in-line inspection tool 10. In one embodiment, the position sensors 20 may comprise one or more odometers 20 positioned to roll along the interior surface of the pipeline and measure the distance traveled by the in-line inspection tool 10.

Figure 2:
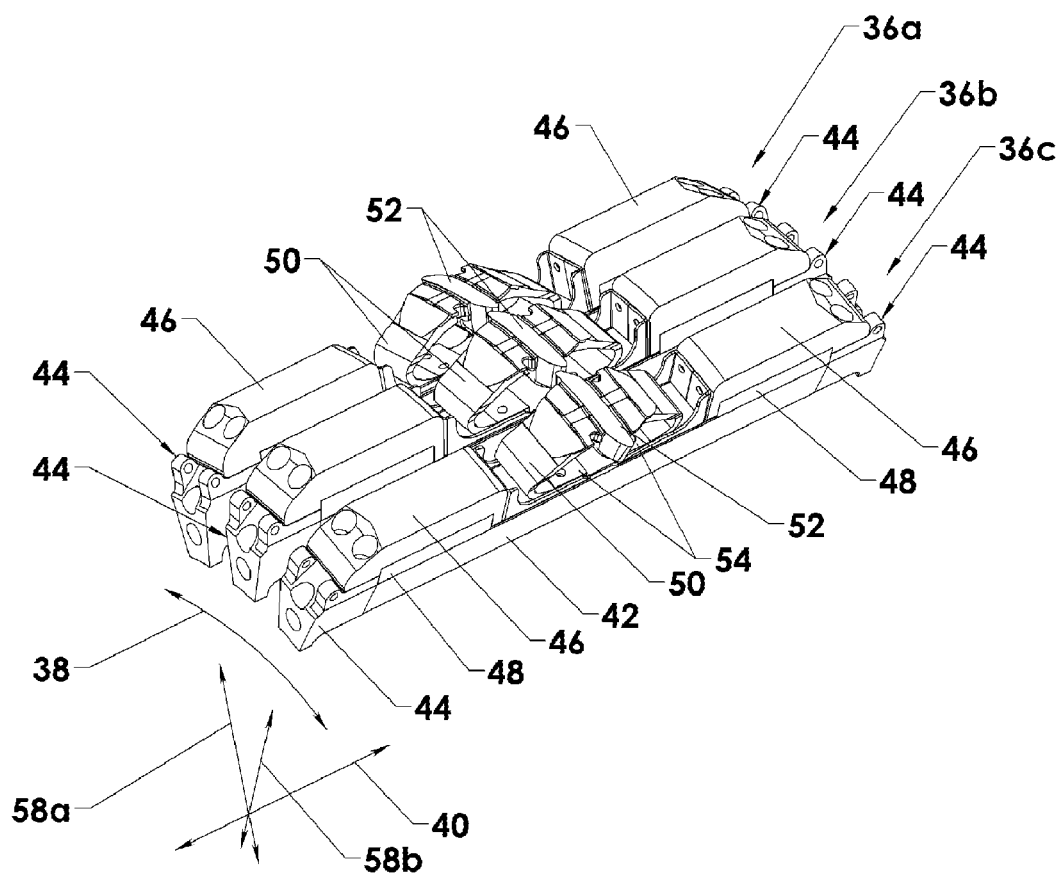
FIG. 2 is a perspective view of selected inspection assemblies positioned with respect to one another as they would be when installed on an in-line inspection tool in accordance with the present invention.

Referring to FIG. 2, in selected embodiments, a primary sensor suite 30 may include a plurality of inspection assemblies 36 distributed circumferentially (i.e., in a circumferential direction 38) about a central axis 40 of an in-line inspection tool 10. Each inspection assembly 36 may include a back bar 42 for supporting the various components of the inspection assembly 36. A linkage mount 44 may be positioned at each end of a back bar 42. Linkages (not shown) may engage an inspection assembly 36 via the linkage mounts 44 and extend therefrom to connect the inspection assembly 36 to an interior cylinder (not shown) forming the back bone of the primary sensor suite 30. Accordingly, inspection assemblies 36 may encircle the interior cylinder.

A back bar 42 may support one or more magnets 48. In certain embodiments, an inspection assembly 36 may include a magnet mount 46 providing an interface between a back bar 42 and a magnet 48. The magnet mount 46 may protect the magnet 48. The magnet mount 46 may also assist in transferring flux into the wall of the pipe being inspected.

In selected embodiments, a back bar 42 may support two magnets 48, one magnet 48 proximate each end thereof. A sensor mount 50 may secure to the back bar 42 at a location between the two magnets 48. The sensor mount 50 may connect a sensor housing 52 to the back bar 42. In certain embodiments, one or more clamps 54 may secure a sensor mount 50 to a back bar 42.

A sensor mount 50 may comprise flexible material. Accordingly, a sensor mount 50 may permit relative motion between a sensor housing 52 and a back bar 42. Constraints such as the magnet mount 46 may be positioned proximate a sensor mount 50 to control or limit certain motion of the sensor mount 50 and sensor housing 52 with respect to the back bar 42. In selected embodiments, a constraint 46 may prevent the sensor housing from contacting or being crushed by the back bar 42. Accordingly, a constraint 46 may provide an additional control over the motion of a sensor housing 52 with respect to a back bar 42.

Figure 3:
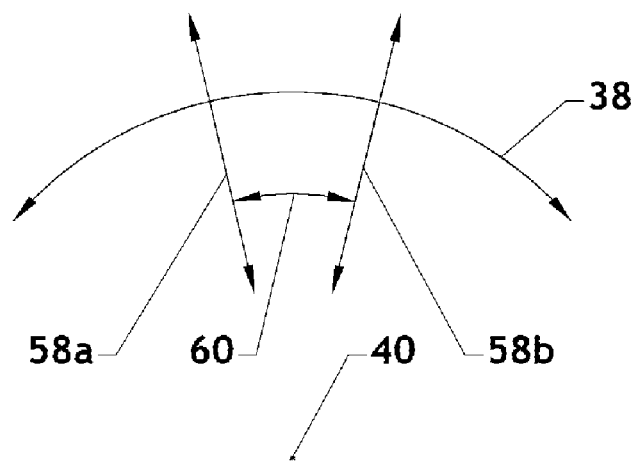
FIG. 3 is a schematic diagram illustrating the changes in circumferential spacing that accompany radial translation of adjacent inspection assemblies in accordance with the present invention.

Referring to FIGS. 2 and 3, inspection assemblies 36 may move in a radial direction 58 with respect to the interior cylinder or main body of an in-line inspection tool 10. This freedom of motion may accommodate changes in the pipe being inspected. For example, features such as bends, constrictions, and changes in the thickness of the wall of the pipe may all affect the interior diameter of a pipeline. Radial movement of an inspection assembly 36 may permit sensor housings 52 to closely track the interior surface of a pipeline in spite of changes in the interior diameter thereof by overlapping and moving closer to one another as their circumferential spacing 60 changes.

Movement in a radial direction 58 changes the spacing in the circumferential direction 38 between adjacent inspection assemblies 36. That is, as two adjacent inspection assemblies 36 move inwardly on respective radial paths 58a, 58b, the distance 60 between those two inspection assemblies 36 decreases. Conversely, as two adjacent inspection assemblies 36 move outward on respective radial paths 58a, 58b, the distance 60 between those two inspection assemblies 36 increases. An inspection assembly 36 in accordance with the present invention may be configured to preserve inspection quality and resolution while accommodating the changes in circumferential spacing caused by radial movement.

For example, in selected embodiments, an inspection assembly 36 may be tapered such that the width on the inner most edge is less than the outward portions of the inspection assembly 36. Additionally, sensor mounts 50 and sensor housings 52 may be configured to accommodate changes in circumferential spacing therebetween.

Figure 4:
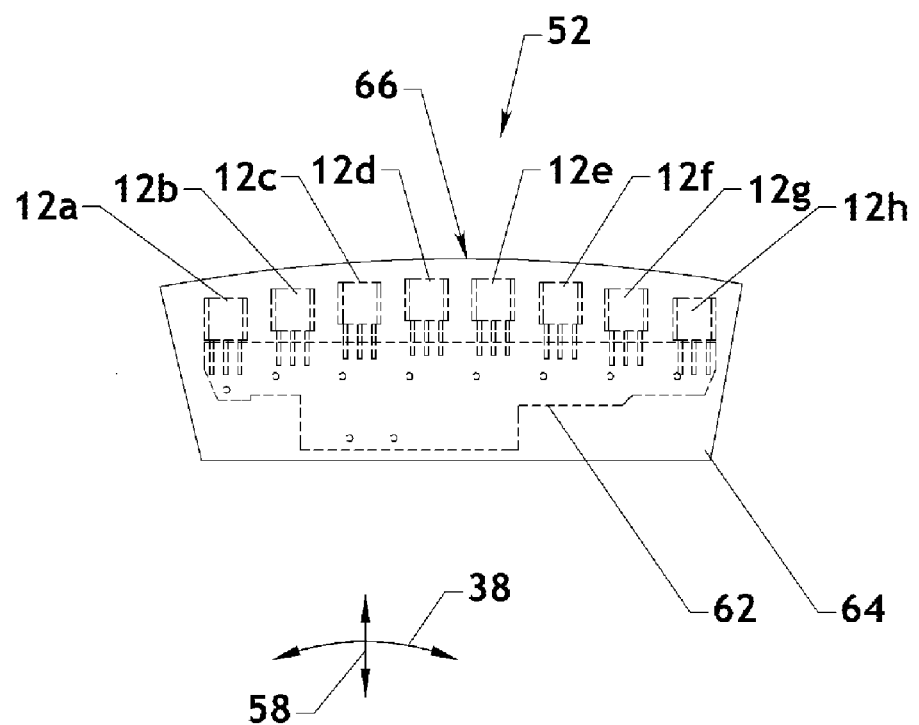
FIG. 4 is an elevation view of one embodiment of a sensor housing in accordance with the present invention with the internal components thereof illustrated using hidden lines.

Referring to FIG. 4, a sensor housing 52 in accordance with the present invention may be substantially rigid. Each sensor housing 52 may house one or more sensors 12. For example, the sensor housing 52 of the illustrated embodiment houses eight sensors 12a, 12b, 12c, 12d, 12e, 12f, 12g, 12h. The sensor 12 or sensors 12 housed within a sensor housing 52 may be mounted on a printed circuit board 62. A sensor housing 52 may contain and protect the sensors 12 and associated circuitry (e.g., circuit board 62) from a pipeline environment.

A sensor housing 52 may be resistant to the pressure and chemicals found in a pipeline environment. In selected embodiments, the components 12, 62 within a sensor housing 52 may be potted in chemical and pressure resistant materials 64 (e.g., selected polymers). The region 66 within a sensor housing 52 between the sensors 52 themselves and the wall of the pipe being inspected may be filled with a similar material. This region 66 may also be capped with a non-magnetic, wear-resistant material. For example the region 66 may be capped with a non-magnetic alloy of select metals.

Figure 5:
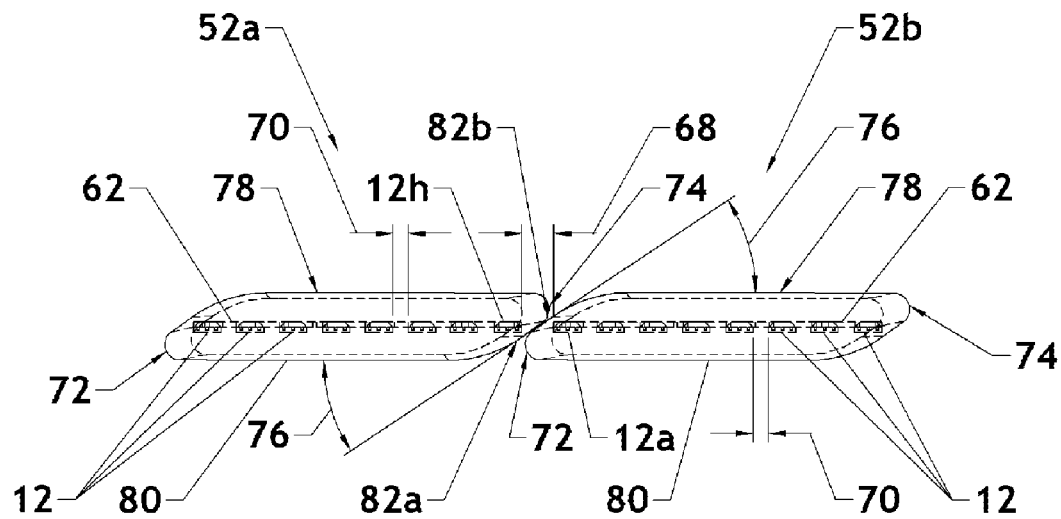
FIG. 5 is a plan view of two adjacent sensor housings in accordance with the present invention with the internal components thereof illustrated using hidden lines.

Referring to FIG. 5, while inspecting a section of pipe having the nominal or expected inner diameter, the spacing 68 between the end sensors 12h and 12a of adjacent sensor housings 52a, 52b may correspond closely with (i.e., substantially match) the spacing 70 between the sensors 12 within a sensor housing 52. Accordingly, sensors 12 may be distributed substantially uniformly around the entire inner circumference of the pipe. Such an arrangement may overcome the inconsistent data collected by irregularly spaced sensors.

Sensor housings 52a and 52b may be placed adjacent one another with the first end 72 of one sensor housing 52b proximate the second end 74 of another sensor housing 52a. In selected embodiments, the first end 72 of a sensor housing 52 may be tapered at an angle 76 from the leading edge 78 of the sensor housing 52. The second end 74 of a sensor housing 52 may also be tapered to the same angle 76, but the taper may be towards the trailing edge 80 of the sensor housing 52. Thus, one end 72 may taper toward a leading edge 78, while the other end 74 tapers toward a trailing edge 80. Accordingly, the end 72 of one sensor housing 52b may overlap the end 74 of an adjacent sensor housing 52a.

As adjacent sensor housings 52a, 52b move inward in a radial direction 58, they may be urged closer to one another. Depending on the characteristics (e.g., angle 76 or the coefficient of friction) of the abutting surfaces 82a, 82b of adjacent sensor housings 52a, 52b, the force urging the two sensor housings 52a, 52b closer together may increase the sensor overlap. In selected embodiments, the abutting surfaces 82a, 82b may be specifically designed to permit or even facilitate this additional overlap.

In selected embodiments, the ability of one sensor housing 52a to slide past and overlap an adjacent sensor housing 52b may be determined by the coefficient of friction between the abutting surfaces 82a, 82b and the angle 76 defining the plane of contact between those surfaces 82a, 82b. In general, the greater the coefficient of friction, the smaller the angle 76 may need to be. One potential solution ensuring that adjacent sensor housings 52 will slide past one another may be where the coefficient of friction times the tangent of angle 76 is greater than zero and less than one (i.e., $0 < \mu \cdot \tan \theta < 1$).

In certain embodiments, the contours of the abutting surfaces 82a, 82b may be such that the angle of the contact therebetween never exceeds the initial angle 76 of contact. Accordingly, in such embodiments, the interaction between the angle of contact and the coefficient of friction is maintained within acceptable bounds.

Figure 6:
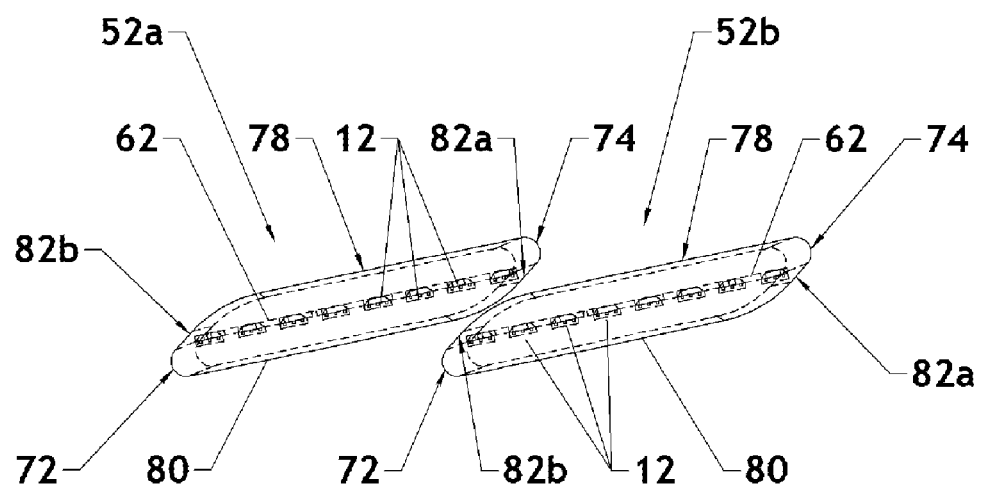
FIG. 6 is a plan view of the two adjacent sensor housings of FIG. 5 rotated to accommodate additional overlap in accordance with the present invention.

Referring to FIG. 6, with additional overlap of adjacent sensor housings 52, each sensor housing 52 may tend to rotate about an axis extending in the radial direction 58. That is, for sensor housings 52 to slide past one another, each sensor housing 52a may rotate to vacate space into which an adjacent sensor housing 52b may extend. The corresponding angles 76 of adjacent contacting surfaces 82a, 82b may ensure that each sensor housing 52 rotates in the same direction.

While overlap of sensor housings 52 may result in multiple sensors 12 tracking the same portion of pipe, this redundancy in constricted spaces (i.e., spaces having an inner diameter less than the nominal or expected inner diameter) may ensure that sensor coverage in non-constricted spaces is uniformly distributed and complete. Even when a sensor housing 52 contains only one sensor 12, the ability of one sensor housing 52 to slide past an adjacent sensor housing 52 may still be beneficial. In such embodiments, a sensor housing 52 in accordance with the present invention may still ensure a uniform distribution without regard to changes in the inner diameter of the pipe being inspected.

In selected embodiments that are not illustrated, sensor housings 52 may not overlap in non-constricted spaces and may overlap as necessary to accommodate relative movement between sensor housings.

Figure 7:
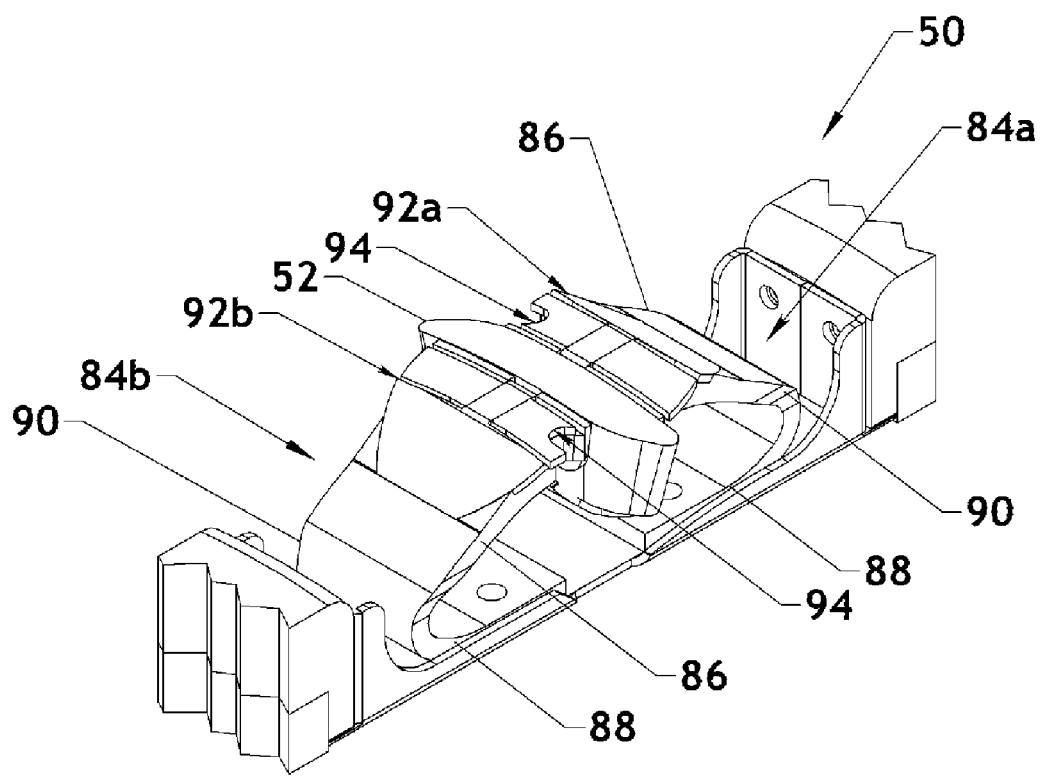
FIG. 7 is a perspective view of a sensor housing secured by a sensor mount in accordance with the present invention.
Figure 7:
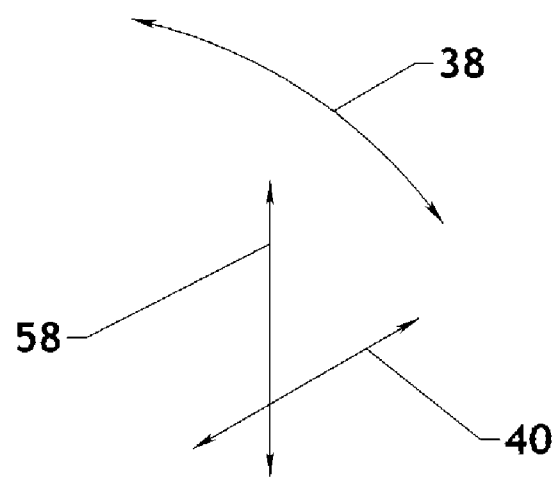

Referring to FIG. 7, in selected embodiments, a sensor mount 50 may be sufficiently flexible to permit a sensor housing 52 held thereby to rotate about an axis extending in the radial direction 58 in the manner described above. A sensor mount 50 may also be sufficiently resilient so that after the constriction in the pipe has been passed, the sensor mount 50 returns the sensor housing 52 held thereby to its original alignment.

In selected embodiments, a sensor mount 50 may include one or more extensions 84 extending from proximate a back bar 42 to hold a sensor housing 52 in the desired position. In certain embodiments, a sensor mount 50 may include a leading extension 84a and a trailing extension 84b. An extension 84 may be formed from a flexible and resilient material. For example, in one embodiment, an extension 84 may be formed of an elastomer (e.g., polyurethane) capable of resisting chemical degradation in the pipeline environment.

In certain embodiments, a leading extension 84*a* and a trailing extension 84*b* may combine to form an arch. A sensor housing 52 may be positioned as if it were the keystone of the arch. The extensions 84*a*, 84*b* may be sized and positioned such that when the in-line inspection tool 10 is outside of a pipe, the apex of the arch formed thereby protrudes slightly into the space that will be occupied by the pipe once inserted therewithin. Accordingly, once inserted within the pipe, the extensions 84*a*, 84*b* may be preloaded in compression, thereby insuring close tracking of the sensor housing 52 along the interior surface of the pipe.

When the geometry of the interior of the pipe changes (e.g., there is a bend, constriction, etc. in the pipe) an extension 84 may resiliently flex, thereby permitting a sensor housing 52 to adjust to the changing geometry. Such adjustments may include translation in a radial direction 58 of a sensor housing 52 with respect to a back bar 42, rotation about an axis extending in a radial direction to permit overlap between adjacent sensor housings 52, tipping or rotation with respect to an axis parallel to the central axis 40 of an in-line inspection tool 10, etc.

Accordingly, a sensor mount 50 may resiliently deflect to allow a sensor housing 52 to move with the six degrees of freedom associated with three dimensional space. Additionally, once the force or obstruction urging such deflection passes, the elastic properties of a sensor mount 50 may return a sensor housing 52 to its original position.

An extension 84 in accordance with the present invention may be shaped in various ways to provide the desired flexibility. For example, in selected embodiments, an extension 84 may include an upper portion 86 and a lower portion 88. The lower portion 88 may secure to a back bar 42. The upper portion may extend toward the sensor housing 52 supported thereby. The extension 84 may also include a bend 90 where the upper portion 86 bends back over the lower portion 88.

In such embodiments, the structural characteristics of the bend 90 may greatly affect the flexibility of the extension 84 as a whole (e.g., its resistance to deflection, rotation, etc.). Accordingly, in selected embodiments, an extension 84 may narrow, thin, or both narrow and thin proximate the bend 90 to increase the flexibility thereof. Such a configuration may permit rotation of a sensor housing 52 about an axis extending in the radial direction 58, yet maintain an arch shape that is sufficiently resistant to deflection in the radial direction 58.

A sensor mount 50 may include one or more wear plates 92. In selected embodiments, a wear plate 92 may slide against the interior surface of a pipe. Accordingly, a wear plate 92 may lower the contact pressure between a sensor housing 52 and the wall of the pipe. This may reduce the wear experienced by the sensor housing 52. Additionally, a wear plate 92 may stabilize a sensor housing 52, lowering the vibration and chatter induced as the sensor housing 52 tracks the interior surface of the pipe.

A wear plate 92 may form the connection between an extension 84 and a sensor housing 52. For example, in selected embodiments, a sensor mount 50 may include a leading wear plate 92*a* and a trailing wear plate 92*b*. The leading wear plate 92*a* may connect a leading extension 84*a* to a leading side of a sensor housing 52. A trailing wear plate 92*b* may connect a trailing extension 84*b* to a trailing side of the sensor housing 52. In selected embodiments, the leading most end of the leading wear plate 92*a*, the trailing most end of the trailing wear plate 92*b*, or both may be tapered. Such tapers may assist in steadying the sensor housing 52 against vibration and chatter as the sensor housing 52 tracks the interior surface of the pipe and may further assist in passing abnormalities in the pipe wall with minimal interference.

Wear plates 92 in accordance with the present invention may be formed of any suitable material. In selected embodiments, a wear plate 92 may be formed of a non-magnetic, wear-resistant metal alloy. For example, a wear plate 92 may be formed of the same material as the cap of a sensor housing 52.

In selected embodiments, a wear plate 92 may be configured to accommodate overlapping between adjacent sensor housings 50. For example, a wear plate 92 may include a void 94 sized and positioned to receive the end 72, 74 of an adjacent sensor housing 52. The void 94 may preclude structural interference between a wear plate 92 and an adjacent sensor housing 52 during overlap.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An in-line inspection tool for inspecting a pipeline while traveling therethrough, the in-line inspection tool comprising:
    a plurality of sensors, each sensor thereof comprising a magnetic flux sensor;
    a plurality of sensor housings, each sensor housing thereof being substantially rigid, comprising a first end and a second end spaced from the first end, and containing a single row of sensors of the plurality of sensors;
    a structure comprising a central axis and a plurality of sensor mounts distributed circumferentially about the central axis;
    the structure, wherein each sensor mount of the plurality of sensor mounts supports a different sensor housing of the plurality of sensor housings; and
    the structure, wherein the plurality of sensor mounts supports the plurality of sensor housings such that
        the first end of each sensor housing of the plurality of sensor housings circumferentially overlaps, and is located axially behind, the second end of an adjacent sensor housing of the plurality of sensor housings, and
        each sensor housing of the plurality of sensor housings is permitted to pivot about a different radial axis intersecting perpendicularly with the central axis.

2. The in-line inspection tool of claim 1, wherein each sensor housing of the plurality of sensor housings houses more than three sensors of the plurality of sensors.

3. The in-line inspection tool of claim 1, wherein the second end of each sensor housing of the plurality of sensor housings is located axially in front of the first end of an adjacent sensor housing of the plurality of sensor housings.

4. The in-line inspection tool of claim 1, wherein the circumferential spacing between adjacent sensors of the plurality of sensors is substantially uniform.

5. The in-line inspection tool of claim 1, wherein each sensor housing of the plurality of sensor housings is substantially identical in shape.

6. The in-line inspection tool of claim 1, wherein each sensor mount of the plurality of sensor mounts is flexible and allows a corresponding sensor housing of the plurality of sensor housings to pivot about the different radial axis.

7. The in-line inspection tool of claim 1, wherein each sensor housing of the plurality of sensor housings houses more than two sensors of the plurality of sensors.

8. The in-line inspection tool of claim 7, wherein the circumferential spacing between all adjacent sensors of the plurality of sensors is substantially uniform.

9. The in-line inspection tool of claim 1, wherein:
the structure further comprises a leading end; and
the distance along the central axis between the leading end and each magnetic flux sensor contained within the plurality of sensor housings is substantially equal.

10. A method comprising:
obtaining an in-line inspection tool comprising
a plurality of sensor housings, each sensor housing thereof being substantially rigid and comprising a first end and a second end spaced from the first end,
a plurality of magnetic flux sensors, at least one sensor thereof being housed within each sensor housing of the plurality of sensor housings,
a structure comprising a central axis and a plurality of sensor mounts distributed circumferentially about the central axis, each sensor mount of the plurality of sensor mounts supporting a different sensor housing of the plurality of sensor housings, and
the plurality of sensor housings wherein the first end of each sensor housing of the plurality of sensor housings is located axially behind the second end of an adjacent sensor housing of the plurality of sensor housings and the second end of each sensor housing of the plurality of sensor housings is located axially in front of the first end of an adjacent sensor housing of the plurality of sensor housings;
introducing the in-line inspection tool into a pipeline;
inspecting, by the in-line inspection tool, the pipeline;
supporting, by the plurality of sensor mounts during at least a portion of the inspecting, the plurality of sensor housings such that the first end of each sensor housing of the plurality of sensor housings circumferentially overlaps the second end of an adjacent sensor housing of the plurality of sensor housings; and
supporting, by the at least one sensor mount of the plurality of sensor mounts during at least a portion of the inspecting, pivoting of a corresponding sensor housing of the plurality of sensor housings about a radial axis intersecting perpendicularly with the central axis.

11. The method of claim 10, further comprising flexing, by each sensor mount of the plurality of sensor mounts during the at least a portion of the inspecting, to permit a corresponding sensor housing of the plurality of sensors housings to rotate about a different radial axis intersecting perpendicularly with the central axis.

12. The method of claim 10, wherein each sensor housing of the plurality of sensor housings houses more than three sensors of the plurality of magnetic flux sensors.

13. The method of claim 12, wherein the obtaining further comprises obtaining an in-line inspection tool wherein the circumferential spacing between all adjacent sensors of the plurality of magnetic flux sensors is substantially uniform.

14. The method of claim 10, wherein the obtaining further comprises obtaining an in-line inspection tool wherein the circumferential spacing between all adjacent sensors of the plurality of magnetic flux sensors is substantially uniform.

15. An in-line inspection tool for inspecting a pipeline while traveling therethrough, the in-line inspection tool comprising:
a plurality of magnetic flux sensors;
a plurality of sensor housings, each sensor housing thereof being substantially rigid, comprising a first end and a second end spaced from the first end, and containing a single row of sensors of the plurality of magnetic flux sensors;
a structure comprising a central axis and a plurality of sensor mounts distributed circumferentially about the central axis; and
the structure, wherein each sensor mount of the plurality of sensor mounts supports a different sensor housing of the plurality of sensor housings such that
the first end of each sensor housing of the plurality of sensor housings circumferentially overlaps the second end of an adjacent sensor housing of the plurality of sensor housings,
the first end of each sensor housing of the plurality of sensor housings is located axially behind the second end of an adjacent sensor housing of the plurality of sensor housings,
the second end of each sensor housing of the plurality of sensor housings is located axially in front of the first end of an adjacent sensor housing of the plurality of sensor housings, and
each sensor housing of the plurality of sensor housings is permitted to pivot about a different radial axis intersecting perpendicularly with the central axis.

16. The in-line inspection tool of claim 15, wherein:
the structure further comprises a leading end; and
the distance along the central axis between the leading end and each magnetic flux sensor contained within the plurality of sensor housings is substantially equal.

\* \* \* \* \*